United States Patent
Dahlmann et al.

(10) Patent No.: US 7,160,507 B2
(45) Date of Patent: Jan. 9, 2007

(54) CORROSION INHIBITORS WITH IMPROVED WATER SOLUBILITY AND IMPROVED FILM PERSISTENCE

(75) Inventors: Uwe Dahlmann, Heidelberg (DE); Michael Feustel, Koengernheim (DE)

(73) Assignee: Clariant GmbH, Frankfurt (DE)

( * ) Notice: Subject to any disclaimer, the term of this patent is extended or adjusted under 35 U.S.C. 154(b) by 493 days.

(21) Appl. No.: 10/483,838

(22) PCT Filed: Jun. 27, 2002

(86) PCT No.: PCT/EP02/07097

§ 371 (c)(1),
(2), (4) Date: Jan. 13, 2004

(87) PCT Pub. No.: WO03/008668

PCT Pub. Date: Jan. 30, 2003

(65) Prior Publication Data

US 2004/0169161 A1    Sep. 2, 2004

(30) Foreign Application Priority Data

Jul. 13, 2001  (DE) ................ 101 34 226

(51) Int. Cl.
 *C23F 11/00* (2006.01)
 *C07C 229/00* (2006.01)
(52) U.S. Cl. .............................. 422/7; 560/170
(58) Field of Classification Search ............ None
See application file for complete search history.

(56) References Cited

U.S. PATENT DOCUMENTS

| | | | |
|---|---|---|---|
| 4,997,912 A | 3/1991 | Wirtz et al. | 530/232 |
| 5,460,728 A | 10/1995 | Klomp et al. | 210/698 |
| 5,523,433 A | 6/1996 | Toney et al. | 554/114 |
| 5,648,575 A | 7/1997 | Klomp et al. | 585/15 |
| 6,025,302 A | 2/2000 | Pakulski | 507/90 |
| 6,152,993 A | 11/2000 | Klomp | 95/153 |
| 6,211,139 B1 | 4/2001 | Keys et al. | 510/504 |
| 6,235,914 B1 | 5/2001 | Steiger et al. | 554/114 |
| 6,261,346 B1 | 7/2001 | Breuer et al. | 106/14.15 |
| 6,372,918 B1 | 4/2002 | Feustel et al. | 548/349.1 |
| 2002/0063241 A1 | 5/2002 | Alink et al. | 252/390 |

FOREIGN PATENT DOCUMENTS

| | | |
|---|---|---|
| DE | 199 30 683 | 1/2001 |
| EP | 0 320 769 | 6/1989 |
| EP | 0 736 130 | 10/1996 |
| EP | 0 824 631 | 2/1998 |
| WO | WO 98/23792 | 6/1998 |
| WO | WO 99/13197 | 3/1999 |
| WO | WO 99/35120 | 7/1999 |
| WO | WO 00/78706 | 12/2000 |
| WO | WO 02/33216 | 4/2002 |

OTHER PUBLICATIONS

Patent Abstracts of Japan, vol. 006, No. 261, Dec. 21, 1982, (English abstract of JP 57 152475, Sanyo Kasei Kogyo and others, Sep. 20, 1982).

*Primary Examiner*—Paul A. Zucker
(74) *Attorney, Agent, or Firm*—Richard P. Silverman

(57) ABSTRACT

The invention relates to an additive and to a method of corrosion inhibition on devices for the recovery and transportation of hydrocarbons in crude oil recovery and processing by adding an effective amount of an inhibitor. The inhibitor comprises an alkoxylated quaternary compounds of the formula 1

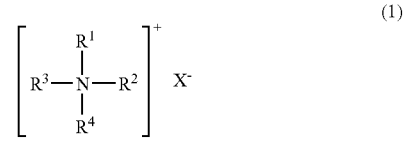

where $R^1$, $R^2$ are independently groups of the formula —(B)—(O—A)$_n$—O—CO—$R^5$ or —(A—O)$_n$—(C)—CO—O—$R^5$, $R^3$ is $C_1$— to $C_{30}$-alkyl or $C_2$— to $C_{30}$-alkenyl, $R^4$ is an organic radical with 1 to 100 carbon atoms optionally containing heteroatoms, $R^5$ is an alkyl or an alkenyl, n is a number from 1 to 20, A is an alkylene group, B is an alkylene group, C is a $C_1$— to $C_6$-alkylene group and X is an anion, used as corrosion inhibitors.

10 Claims, No Drawings

CORROSION INHIBITORS WITH IMPROVED WATER SOLUBILITY AND IMPROVED FILM PERSISTENCE

The present invention relates to an additive and to a method of corrosion inhibition on devices for the recovery and transportation of hydrocarbons in crude oil recovery and processing.

In industrial processes where metals come into contact with water or else with oil-water two-phase systems, there is a risk of corrosion. This risk is particularly marked in salt water systems as arise in crude oil production and processing processes. Without special additives for protecting the equipment used, the exploitation of a field and the processing of the crude oil are not possible.

Although such corrosion inhibitors have been known for a long time, they are not optimal in many respects. Many products, e.g. amides/imidazolines from fatty acids and polyamines, are too soluble in oil and are thus present only in a low concentration in the corrosive water phase due to poor partition equilibria (partitioning). Accordingly, these are effective as corrosion inhibitors only to a low degree or only at a high concentration.

DE-A-199 30 683 describes amidamines/imidazolines which are obtained by reacting alkyl polyglycol ether carboxylic acids with polyamines and, due to their structure, have very good water solubility and thus have corrosion protection improved by good partitioning.

Quaternary alkylammonium compounds (quats) represent alternative corrosion inhibitors in the prior art which, as well as the corrosion-inhibiting properties, also have biostatic properties. Despite an improved water solubility, the quats exhibit, for example in comparison to the imidazolines, a significantly reduced film persistence and therefore likewise only lead to effective corrosion protection in a relatively high concentration. Furthermore, the poor biodegradability limits their use in ecologically sensitive fields of application.

U.S. Pat. No. 5,523,433 discloses compounds of the formula

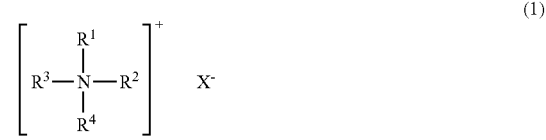

in which $R^a$ and $R^b$ may be $C_{12}$- to $C_{22}$-alkyl radicals and $R^1$ and $R^2$ may be $C_1$- to $C_4$-alkyl radicals. The document discloses the suitability of such compounds as a constituent of fabric softeners.

EP-B-0 736 130, EP-B-0 824 631, U.S. Pat. No. 5,648,575 and WO-99/13197 disclose methods of inhibiting gas hydrates using alkoxylated alkylammonium compounds.

U.S. Pat. No. 6,025,302 discloses polyether amine ammonium compounds as gas hydrate inhibitors whose ammonium nitrogen atom carries three alkyl substituents as well as the polyether amine chain.

WO-00/78 706 describes quaternary ammonium compounds but which do not carry carbonyl radicals. The use as corrosion inhibitors is not disclosed.

An object of the present invention was thus to find novel corrosion inhibitors which, coupled with consistently good or improved corrosion protection as well as an optimized water solubility, a more rapid film formation and thus improved film persistence, also offer improved biodegradability compared with the corrosion inhibitors of the prior art.

Surprisingly, it has now been found that doubly N-alkoxylated and carbonylated ammonium salts have excellent effectiveness as corrosion inhibitors, and also exhibit improved film persistence and good biodegradability.

The invention thus provides for the use of compounds of the formula 1

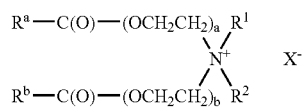 (1)

in which $R^1$, $R^2$, independently of one another, are radicals of the formulae

 (2)

or

 (3)

$R^3$ is $C_1$- to $C_{30}$-alkyl or $C_2$- to $C_{30}$-alkenyl
$R^4$ is an organic radical having 1 to 100 carbon atoms which optionally contains heteroatoms
$R^5$ is $C_1$- to $C_{30}$-alkyl or $C_2$- to $C_{30}$-alkenyl
n is a number from 1 to 20
A is a $C_2$- to $C_4$-alkylene group,
B is a $C_1$- to $C_{10}$-alkylene group,
C is a $C_1$- to $C_6$-alkylene group and
X is an anion as corrosion inhibitors.

The invention further provides a method of inhibiting corrosion at metal surfaces, in particular of iron-containing metals, by adding at least one compound of the formula 1 to a corrosive system which is in contact with the metal surfaces.

The invention further provides the compounds of the formula (1), but where those compounds in which $R^4$ does not contain a heteroatom and $R^1$ and $R^2$ simultaneously have the meaning given in formula (2) are excluded.

For the purposes of this invention, corrosive systems are preferably liquid/liquid or liquid/gaseous multiphase systems consisting of water and hydrocarbons which contain, in free and/or dissolved form, corrosive constituents, such as salts and acids. The corrosive constituents can also be gaseous, such as, for example, hydrogen sulfide and carbon dioxide. For the purposes of this invention, hydrocarbons are organic compounds which are constituents of crude oil/natural gas, and secondary products thereof.

A can be straight-chain or branched and is preferably an ethylene or propylene group, in particular an ethylene group. The alkoxy groups referred to by $(A—O)_n$ can also be mixed alkoxy groups.

B can be straight-chain or branched and is preferably a $C_2$- to $C_4$-alkylene group, in particular an ethylene or propylene group.

C can be straight-chain or branched and is preferably a $C_2$- to $C_4$-alkylene group, in particular a methylene or ethylene group.

n is preferably a number between 2 and 6.

$R^5$ is preferably an alkyl or alkenyl group having 2 to 24 carbon atoms, in particular 4 to 12 carbon atoms.

$R^3$ is preferably an alkyl or alkenyl group from 2 to 12 carbon atoms, in particular those groups having 4 to 8 carbon atoms and specifically butyl groups.

$R^4$ can be any organic radical which contains 1 to 100 carbon atoms and which can contain heteroatoms. If $R^4$ contains heteroatoms, then these are preferably nitrogen or oxygen atoms or both, preferably both. The nitrogen atoms can be in quaternized form.

In a further preferred embodiment, $R^4$ comprises 1 to 20 alkoxy groups derived from $C_2$- to $C_4$-alkylene oxide, in particular from ethylene oxide and/or propylene oxide. In particular, $R^4$ can be a radical according to formula (2) or (3).

In a particularly preferred embodiment, $R^4$ corresponds to a radical of the formula (4)

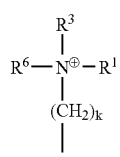

(4)

where the bonding to the nitrogen atom in formula 1 takes place by the free valence of the $(CH_2)_k$ group. In formula (4), $R^6$ is a radical of the formulae

(2)

or

(3)

or $C_1$- to $C_{30}$-alkyl or $C_2$- to $C_{30}$-alkenyl, in each case with the preferred ranges given above for A, B, n, $R^3$ and $R^5$. k is 2 or 3, $R^1$ and $R^3$ have the meanings given above.

Suitable counterions X are all ions which do not impair the solubility of the compounds of the formula (1) in the corrosive organic-aqueous mixed phases. Such counterions are, for example, methylsulfate ions (methosulfate) or halide ions.

Particularly preferred compounds (shown without counterions) correspond to the formulae (5) to (8)

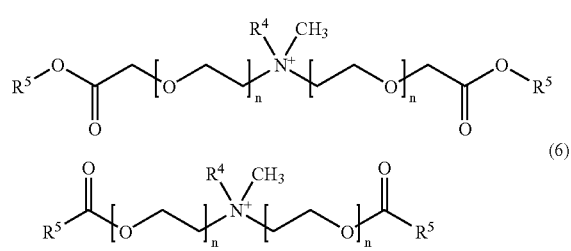

(5)

(6)

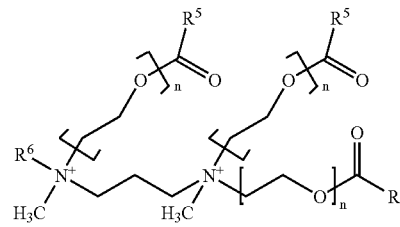

(7)

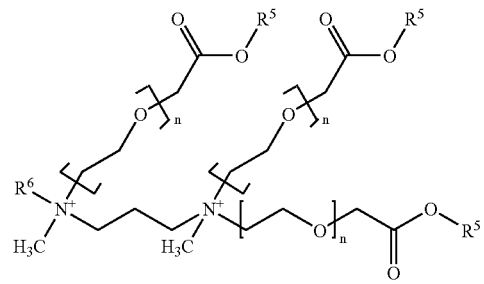

(8)

The compounds according to the invention can be used on their own or in combination with other known corrosion inhibitors. In general, the amount of corrosion inhibitor according to the invention used is sufficient to provide adequate corrosion protection under the given conditions. Preferred use concentrations, based on the pure compounds according to the invention, are 5 to 5000 ppm, preferably 10 to 1000, in particular 15 to 150 ppm.

Particularly suitable corrosion inhibitors are also mixtures of the products according to the invention with other corrosion inhibitors known from the literature, such as amide amines and/or imidazolines from fatty acids and polyamines and salts thereof, quaternary ammonium salts, oxyethylated/oxypropylated amines, amphoglycinates and ampho-propionates, betaines or compounds described in DE-A-19 930 683.

The compounds according to the invention can be prepared by reacting alkoxylated alkylamines or alkylaminoalkyleneamines with monochloro-carboxylic acids to give the corresponding ether carboxylic acids and subsequent esterification with alkanols. On the other hand, the bis-alkoxylated monoalkylamines or alkylaminoalkyleneamines can be reacted directly with carboxylic acids and derivatives thereof, such as anhydrides, carbonyl chlorides or esters thereof, to give the esters according to the invention. The quaternization is then carried out with suitable alkylating agents.

The preparation of alkoxylated alkylamines or alkylaminoalkyleneamines; is described in the prior art.

The basis of the alkoxylated alkylamines used are alkylamines having $C_1$- to $C_{30}$-alkyl radicals or $C_2$- to $C_{30}$-alkenyl radicals, preferably $C_3$- to $C_8$-alkylamines. Suitable alkylamines are, for example, n-butylamine, isobutylamine, pentylamine, hexylamine, octylamine, cyclopentylamine, cyclohexylamine.

The basis of the alkoxylated alkylaminoalkyleneamines used are aminoalkyleneamines having $C_1$- to $C_{30}$-alkyl radicals or $C_2$- to $C_{30}$-alkenyl radicals and k=2 or 3. Suitable aminoalkyleneamines are, for example, fatty alkylpropylenediamines, such as tallow fatty propylenediamine, stearylpropylenediamine, oleylpropylenediamine, laurylpropylenediamine, dodecylpropylenediamine and octylpropylenediamine.

The alkylamines or alkylaminoalkyleneamines are generally reacted with ethylene oxide, propylene oxide, butylene oxide or mixtures of different such alkylene oxides, where ethylene oxide or mixtures of ethylene oxide and propylene oxide are preferred. Based on alkylamine or alkylaminoalkyleneamines, 1–40 mol of alkylene oxide are supplied, preferably 1–12 mol.

The alkoxylation takes place without a diluent, but can also be carried out in solution. Suitable solvents for the alkoxylation are inert ethers, such as dioxane, tetrahydrofuran, glyme, diglyme and MPEGs.

In general, the alkoxylation in the first reaction step is carried out uncatalyzed up to >95% by weight of tert-nitrogen. Higher alkoxylation takes place following the addition of basic compounds as catalysts. Basic compounds which can be used are alkaline earth metal/alkali metal hydroxides or alkoxides (sodium methoxide, sodium ethoxide, potassium tert-butoxide), but preference is given to alkali metal hydroxides, particularly sodium hydroxide or potassium hydroxide.

For the preparation of the compounds according to the invention, in a subsequent reaction step the amine-oxyethylate mixtures are reacted with a chlorocarboxylic acid derivative and a base, preferably dry sodium chloroacetate and sodium hydroxide. This may involve reacting the oxyethylate mixture with 100 to 150 mol % of sodium chloroacetate at 30 to 100° C. and, simultaneously or subsequently, adding solid sodium hydroxide or potassium hydroxide, so that the sum of the base already present in the oxyethylate mixture and the amount of base additionally added corresponds to the amount of sodium chloroacetate. The amount of base already present from the reaction with the alkylene oxide can thus be utilized directly for the subsequent Williamson synthesis and does not, as in the synthesis of a standard oxyethylate, have to be washed out.

Subsequently to the alkylation reaction, the alkoxylated amine ether carboxylic acid alkali metal salts are converted into the free ether carboxylic acid. For this purpose, the mixture is acidified to pH<3 with a strong mineral acid (hydrochloric acid, sulfuric acid) and the ether carboxylic acid is separated off as the upper phase while hot by phase separation above its cloud point.

The subsequent esterification of the alkoxylated amine ether carboxylic acids generally takes place by direct reaction of the free acid with corresponding alcohols at temperatures of 100–200° C., where the water of reaction is removed by distillation. The esterification can be accelerated by adding suitable acidic catalysts with a $pK_a$ value of less than or equal to 5 or by removing the water of reaction azeotropically using suitable solvents. Suitable catalysts are, for example, sulfonic acid and alkylstannic acids.

For the esterification of the alkoxylated amine ether carboxylic acids, use is made of alcohols having $C_4$- to $C_{30}$-alkyl radicals or $C_4$- to $C_{30}$-alkenyl radicals, preferably fatty alcohols. Suitable alcohols are, for example, 2-ethylhexanol, octanol, decanol, lauryl alcohol, palmityl alcohol, stearyl alcohol and oleyl alcohol.

The compounds according to the invention can also be prepared by esterification of the amine/oxyethylate mixtures with carboxylic acids and derivatives thereof, such as carbonyl chlorides, carboxylic anhydrides and carboxylic acid esters. The esterification with free carboxylic acids takes place at temperatures of 100–200° C., where the water of reaction is removed by distillation. The esterification can be accelerated by adding suitable acidic catalysts with a $pK_a$ value of less than or equal to 5 or by removing the water of reaction azeotropically using suitable solvents. Suitable carboxylic acids are acetic acid, propionic acid, caproic acid, caprylic acid, 2-ethylhexanoic acid and fatty acids or anhydrides thereof, methyl esters and chlorides.

The preparation of the compounds according to the invention then takes place by quaternization of the tertiary nitrogen atoms with a suitable alkylating agent at 50 to 150° C. Suitable alkylating agents are alkyl halides and alkyl sulfates, preferably methylene chloride, butyl bromide and dimethyl sulfate.

EXAMPLES a) General Procedure for the Preparation of Alkoxylated Amine Ether Carboxylic Acids 2 mol of the corresponding alkoxylated amine or 1 mol of the corresponding alkoxylated diamine (according to OH number) were initially introduced into a stirred apparatus under nitrogen blanketing and heated to 40° C. Then, 650 g (4.8 mol) of sodium chloroacetate were introduced for alkoxylated monoamines, or 488 g (3.6 mol) of sodium chloroacetate were introduced for alkoxylated diamines, and the reaction mixture was heated to 50° C.

After 30 min in each case, 192 g (4.8 mol) or 144 g (3.6 mol) of NaOH microprills were added in 6 portions such that the temperature does not exceed 55° C. The mixture was after-reacted for 2 h at 70° C. 10% strength hydrochloric acid was then metered in until a pH<3 was reached. The mixture was then heated to 95° C. and transferred to a heatable stirred apparatus with bottom drain outlet. Phase separation was carried out after 15 min at 105–108° C. The aqueous lower phase was discarded. With products which cannot be separated by heating to above the cloud point, the water of reaction was removed by distillation and the salt which precipitated out was filtered off.

Example 1 n-butylamine+6 EO-ECA 699 g of n-butylamine+6 EO (OH number: 321.1 mg of KOH/g) gave 970 g of n-butylamine+6 EO-ECA with AN=221.5 mg of KOH/g (corresponds to 91.9% conversion) and bas.—N=3.00%.

Example 2 caprylamine+6 EO-ECA 801 g of caprylamine+6 EO (OH number: 280.1 mg of KOH/g) gave 1045 g of caprylamine+6 EO-ECA with AN=200.9 mg of KOH/g (corresponds to 92.5% conversion) and bas.—N=2.69%.

Example 3 caprylamine+10 EO-ECA 1147 g of caprylamine+10 EO (OH number: 195.7 mg of KOH/g) gave 1412 g of caprylamine+10 EO-ECA with AN=144.9 mg of KOH/g (corresponds to 89.0% conversion) and bas.—N=1.90%.

Example 4 tallow fatty propylenediamine+10 EO-ECA 768 g of tallow fatty propylenediamine+10 EO (OH number: 219.2 mg of KOH/g) gave 970 g of tallow fatty propylenediamine+10 EO-ECA with AN=156.7 mg of KOH/g (corresponds to 87.7% conversion) and bas.—N=2.88%.

Example 5 tallow fatty propylenediamine+25 EO-ECA 1316 g of tallow fatty propylenediamine+25 EO (OH number: 127.9 mg of KOH/g) gave 1700 g of tallow fatty propylenediamine+25 EO-ECA with AN=85.0 mg of KOH/g (corresponds to 84.0% conversion) and bas.—N=1.49%.

Example 6 tallow fatty propylenediamine+30 EO-ECA 1699 g of tallow fatty propylenediamine+30 EO (OH number: 99.1 mg of KOH/g) gave 2043 g of tallow fatty propylenediamine+30 EO-ECA with AN=66.5 mg of KOH/g (corresponds to 80.9% conversion) and bas.—N=1.30%.

Example 7 tallow fatty propylenediamine+35 EO-ECA 1919 g of tallow fatty propylenediamine+35 EO (OH number: 87.7 mg of KOH/g) gave 2301 g of tallow fatty propylenediamine+35 EO-ECA with AN=63.2 mg of KOH/g (corresponds to 85.5% conversion) and bas.—N=1.19%.

Example 8

(laurylpropylenediamine+10 EO-ECA)

673 g of laurylpropylenediamine+10 EO (OH number: 250.0 mg of KOH/g) gave 1071 g of laurylpropylenediamine+10 EO-ECA with AN=149.2 mg of KOH/g (corresponds to 90.5% conversion) and bas.—N=2.54%.

Example 9

(laurylpropylenediamine+30 EO-ECA)

1639 g of laurylpropylenediamine+30 EO (OH number: 102.7 mg of KOH/g) gave 1964 g of laurylpropylenediamine+30 EO-ECA with AN=82.3 mg of KOH/g (corresponds to 97.1% conversion) and bas.—N=1.40%.

b) General Procedure for the Preparation of Alkoxylated Amine Ether Carboxylic Acid Alkyl Esters 1 mol or 0.5 mol (according to AN) of the corresponding alkoxylated alkylamineether carboxylic acid or alkylenediamineether carboxylic acid, respectively, were initially introduced into a stirred apparatus with nitrogen blanketing and an excess (about 1.5 mol equivalents per carboxylic acid function) of alcohol was added. Following the addition of 0.5% by weight of FASCAT 4100 (butylstannic acid), the mixture was heated to 100° C. to 180° C., during which the water of reaction distilled off. After a reaction time of 8 h or after an acid number of AN<5 mg of KOH/g had been reached, the reaction was complete and excess alcohol and residual water were removed by distillation under reduced pressure.

Example 10 n-butylamine+6 EO 2-ethylhexyl ECA ester 507 g of n-butylamine+6 EO-ECA and 391 g of 2-ethylhexanol gave 707 g of n-butylamine+6 EO 2-ethylhexyl ECA ester with AN=4.1 mg of KOH/g and VN=158.1 mg of KOH/g (corresponds to 97.4% conversion).

Example 11 caprylamine+6 EO 2-ethylhexyl ECA ester 559 g of caprylamine+6 EO-ECA and 391 g of 2-ethylhexanol gave 738 g of caprylamine+6 EO 2-ethylhexyl ECA ester with AN=3.3 mg of KOH/g and VN=147.0 mg of KOH/g (corresponds to 97.8% conversion).

Example 12 caprylamine+10 EO 2-ethylhexyl ECA ester 774 g of caprylamine+10 EO-ECA and 391 g of 2-ethylhexanol gave 999 g of caprylamine+10 EO 2-ethylhexyl ECA ester with AN=4.8 mg of KOH/g and VN=114.1 mg of KOH/g (corresponds to 95.8% conversion).

Example 13 tallow fatty propylenediamine+10 EO 2-ethylhexyl ECA ester 537 g of tallow fatty propylenediamine+10 EO-ECA and 293 g of 2-ethylhexanol gave 688 g of tallow fatty propylenediamine+10 EO 2-ethylhexyl ECA ester with AN=4.7 mg of KOH/g and VN=121.3 mg of KOH/g (corresponds to 96.1% conversion).

Example 14 tallow fatty propylenediamine+25 EO ethylhexyl ECA ester 990 g of tallow fatty propylenediamine+25 EO-ECA and 293 g of 2-ethylhexanol gave 1068 g of tallow fatty propylenediamine+25 EO 2-ethylhexyl ECA ester with AN=6.7 mg of KOH/g and VN=74.6 mg of KOH/g (corresponds to 91.0% conversion).

Example 15 tallow fatty propylenediamine+30 EO ethylhexyl ECA ester 1266 g of tallow fatty propylenediamine+30 EO-ECA and 293 g of 2-ethylhexanol gave 1374 g of tallow fatty propylenediamine+30 EO 2-ethylhexyl ECA ester with AN=3.5 mg of KOH/g and VN=61.7 mg of KOH/g (corresponds to 94.3% conversion).

Example 16 tallow fatty propylenediamine+35 EO dodecyl ECA ester 1332 g of tallow fatty propylenediamine+35 EO-ECA and 419 g of lauryl alcohol gave 1523 g of tallow fatty propylenediamine+35 EO 2-dodecyl ECA ester with AN=4.9 mg of KOH/g and VN=54.2 mg of KOH/g (corresponds to 90.9% conversion).

Example 17 laurylpropylenediamine+10 EO 2-ethylhexyl ECA ester)

564 g of laurylpropylenediamine+10 EO-ECA and 293 g of 2-ethylhexanol gave 703 g of laurylpropylenediamine+10 EO 2-ethylhexyl ECA ester with AN=3.6 mg of KOH/g and VN=117.9 mg of KOH/g (corresponds to 96.9% conversion).

Example 18 laurylpropylenediamine+30 EO dodecyl ECA ester 1023 g of laurylpropylenediamine+30 EO-ECA and 419 g of lauryl alcohol gave 1213 g of laurylpropylenediamine+30 EO dodecyl ECA ester with AN=6.0 mg of KOH/g and VN=66.8 mg of KOH/g (corresponds to 91.0% conversion).

c) General Procedure for the Preparation of Alkoxylated Aminecarboxylic Acid Esters by Reaction with Carboxylic Acids 1 mol or 0.5 mol (according to OH number) of the corresponding alkoxylated alkylamine or alkylenediamine, respectively, was initially introduced into a stirred apparatus with nitrogen blanketing, and 1 mol equivalent (depending on OH function) of the corresponding carboxylic acid was added (depending on OH function). Following the addition of 0.5% by weight of FASCAT 4100 (butylstannic acid), the mixture was heated to 100° C. to 200° C., during which the water of reaction distilled off. After a reaction time of 8 h or after an acid number of AN<10 mg of KOH/g had been reached, the reaction was complete and residual water was removed by distillation under reduced pressure.

d) General Procedure for the Preparation of Alkoxylated Aminecarboxylic Acid Esters by Reaction with Carboxylic Anhydrides 1 mol or 0.5 mol (according to OH number) of the corresponding alkoxylated alkylamine or alkylenediamine, respectively, was initially introduced into a stirred apparatus under nitrogen blanketing, and 1 mol equivalent of the corresponding carboxylic anhydride (depending on OH function) was added. The mixture was heated to 100° C. to 150° C. After a reaction time of 8 h at this reaction temperature, the liberated carboxylic acid was distilled off.

Example 19 n-butylamine+6 EO acetic acid ester 349 g of n-butylamine+6 EO (OH number: 321.1 mg of KOH/g) and 204 g of acetic anhydride gave 434 g of n-butylamine+6 EO acetic acid ester with AN=0.1 mg of KOH/g and VN=260.2 mg of KOH/g.

Example 20 n-butylamine+6 EO propionic acid ester 349 g of n-butylamine+6 EO (OH number: 321.1 mg of KOH/g) and 260 g of propionic anhydride gave 465 g of n-butylamine+6 EO propionic acid ester with AN=0.7 mg of KOH/g and VN=244.9 mg of KOH/g.

Example 21 n-butylamine+6 EO 2-ethylhexanoic acid ester 349 g of n-butylamine+6 EO (OH number: 321.1 mg of KOH/g) and 288 g of 2-ethylhexanoic acid gave 594 g of n-butylamine+6 EO 2-ethylhexanoic acid ester with AN=6.4 mg of KOH/g and VN=191.8 mg of KOH/g.

Example 22 n-butylamine+6 EO isononanoic acid ester 349 g of n-butylamine+6 EO (OH number: 321.1 mg of KOH/g) and 316.5 g of isononanoic acid gave 636 g of n-butylamine+6 EO isononanoic acid ester with AN=5.9 mg of KOH/g and VN=183.3 mg of KOH/g.

Example 23 caprylamine+6 EO acetic acid ester 401 g of caprylamine+6 EO (OH number: 280.1 mg of KOH/g) and 204 g of acetic anhydride gave 484 g of caprylamine+6 EO acetic acid ester with AN=0.2 mg of KOH/g and VN=231.5 mg of KOH/g.

Example 24 caprylamine+6 EO propionic acid ester 401 g of caprylamine+6 EO (OH number: 280.1 mg of KOH/g) and 260 g of propionic anhydride gave 517 g of caprylamine+6 EO propionic acid ester with AN=0.4 mg of KOH/g and VN=220.8 mg of KOH/g.

Example 25 caprylamine+6 EO 2-ethylhexanoic acid ester 401 g of caprylamine+6 EO (OH number: 280.1 mg of KOH/g) and 288 g of 2-ethylhexanoic acid gave 643 g of caprylamine+6 EO 2-ethylhexanoic acid ester with AN=8.1 mg of KOH/g and VN=179.6 mg of KOH/g.

Example 26 caprylamine+6 EO isononanoic acid ester 401 g of caprylamine+6 EO (OH number: 280.1 mg of KOH/g) and 316.5 g of isononanoic acid gave 672 g of caprylamine+6 EO isononanoic acid ester with AN=4.1 mg of KOH/g and VN=167.2 mg of KOH/g.

Example 27 tallow fatty propylenediamine+25 EO propionic acid ester 658 g of tallow fatty propylenediamine+25 EO (OH number: 127.9 mg of KOH/g) and 195 g of propionic anhydride gave 750 g of tallow fatty propylenediamine+25 EO propionic acid ester with AN=0.7 mg of KOH/g and VN=114.3 mg of KOH/g.

Example 28 tallow fatty propylenediamine+25 EO 2-ethylhexanoic acid ester 658 g of tallow fatty propylenediamine+25 EO (OH number: 127.9 mg of KOH/g) and 216 g of 2-ethylhexanoic acid gave 859 g of tallow fatty propylenediamine+25 EO 2-ethylhexanoic acid ester with AN=8.6 mg of KOH/g and VN=107.6 mg of KOH/g.

Example 29 tallow fatty propylenediamine+25 EO Coconut Fatty acid ester)

658 g of tallow fatty propylenediamine+25 EO (OH number: 127.9 mg of KOH/g) and 310 g of coconut fatty acid (AN=271.3 mg of KOH/g) gave 951 g of tallow fatty propylenediamine+25 EO coconut fatty acid ester with AN=4.5 mg of OH/g and VN=93.9 mg of KOH/g.

Example 30 laurylpropylenediamine+30 EO Coconut Fatty acid ester 820 g of laurylpropylenediamine+30 EO (OH number: 102.7 mg of KOH/g) and 310 g of coconut fatty acid (AN=271.3 mg of KOH/g) gave 1107 g of laurylpropylenediamine+30 EO coconut fatty acid ester with AN=3.6 mg of KOH/g and VN=79.9 mg of KOH/g.

e) General Procedure for the Quaternization of the Alkoxylated Amine Ether Carboxylic Acid Alkyl Esters or the Alkoxylated Aminecarboxylic Acid Esters 0.5 mol (according to VN number) of the corresponding alkoxylated amine ether carboxylic acid alkyl ester or of the alkoxylated aminecarboxylic acid ester was initially introduced into a stirred apparatus with nitrogen blanketing and heated to 60° C. 0.4 mol of dimethyl sulfate was added dropwise to this such that the reaction temperature did not exceed 80–90° C. reaction mixture was then after-stirred for 3 h at 90° C. After this procedure, the compounds, described by examples 10 to 30, were quaternized (examples 31 to 51, as listed in table 1 and 2).

Effectiveness of the Compounds According to the Invention as Corrosion Inhibitors The compounds according to the invention were tested as corrosion inhibitors in the Shell wheel test. Coupons made of C-steel (DIN 1.1203 with a surface area of 15 cm$^2$) were dipped into a saltwater/petroleum mixture (9:1.5% strength NaCl solution adjusted to pH 3.5 with acetic acid) and exposed to this medium at a circulatory rate of 40 rpm at 70° C. for 24 hours. The concentration of the inhibitor was 50 ppm of a 40% solution of the inhibitor. The protection values were calculated from the mass decrease of the coupons, based on a blank value.

In the tables below, "comparison" refers to a residue amine-quat based on dicocoalkyldimethylammonium chloride (corrosion inhibitor of the prior art).

TABLE 1

(SHELL wheel test)

| Example | Corrosion inhibitor | Ø Protection % |
|---|---|---|
| Comparison | | 36.0 |
| 31 | Quat from example 10 | 86.0 |
| 32 | Quat from example 11 | 88.6 |
| 33 | Quat from example 12 | 79.2 |
| 34 | Quat from example 13 | 65.3 |
| 35 | Quat from example 14 | 51.8 |
| 36 | Quat from example 15 | 47.7 |
| 37 | Quat from example 16 | 76.3 |
| 38 | Quat from example 17 | 64.0 |
| 39 | Quat from example 18 | 81.9 |
| 40 | Quat from example 19 | 32.4 |
| 41 | Quat from example 20 | 32.8 |
| 42 | Quat from example 21 | 86.0 |
| 43 | Quat from example 22 | 85.0 |
| 44 | Quat from example 23 | 49.9 |
| 45 | Quat from example 24 | 52.3 |
| 46 | Quat from example 25 | 87.1 |
| 47 | Quat from example 26 | 90.4 |
| 48 | Quat from example 27 | 35.2 |
| 49 | Quat from example 28 | 37.1 |
| 50 | Quat from example 29 | 89.6 |
| 51 | Quat from example 30 | 84.6 |

The products were also tested in the LPR test (test conditions analogous to ASTM D 2776).

TABLE 2

(LPR test)

| | | Protection after [%] | | |
|---|---|---|---|---|
| Example | Corrosion inhibitor | 10 min | 30 min | 60 min |
| Comparison | | 53.9 | 61.2 | 73.7 |
| 52 | Example 31 | 74.3 | 84.8 | 87.0 |
| 53 | Example 32 | 78.4 | 86.1 | 92.3 |
| 54 | Example 33 | 70.2 | 74.7 | 81.0 |
| 55 | Example 37 | 51.9 | 65.6 | 74.9 |
| 56 | Example 39 | 53.5 | 65.9 | 75.2 |
| 57 | Example 42 | 67.7 | 75.6 | 79.0 |
| 58 | Example 43 | 76.1 | 83.6 | 86.7 |
| 59 | Example 46 | 78.0 | 85.7 | 87.9 |
| 60 | Example 47 | 80.2 | 87.2 | 93.4 |
| 61 | Example 50 | 53.9 | 67.1 | 78.6 |
| 62 | Example 51 | 78.0 | 85.7 | 87.9 |

As can be seen from the above test results, the products according to the invention have very good corrosion protection properties at a low concentration. The compounds are biodegradable, as shown below.

TABLE 3

(Storm test in accordance with OECD 301 B)

| Example | Corrosion inhibitor | Biodegradability in % |
|---|---|---|
| Comparison | | 28 |
| 63 | Example 32 | 46 |
| 64 | Example 46 | 52 |
| 65 | Example 47 | 38 |
| 66 | Example 51 | 55 |

The invention claimed is:
1. A method of inhibiting corrosion at metal surfaces comprising the steps of:
providing a corrosive system which is in contact with a metal surface;
providing compounds of the formula 1

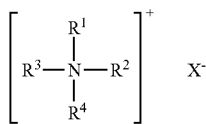  (1)

in which

R¹, R², is a radical of the formula

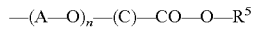  (3)

R³ is $C_1$- to $C_{30}$-alkyl or $C_2$- to $C_{30}$-alkenyl

R⁴ is an organic radical having 1 to 100 carbon atoms which optionally contains heteroatoms R⁵ is $C_1$- to $C_{30}$-alkyl or $C_2$- to $C_{30}$-alkenyl n is a number from 1 to 20

A is a $C_2$- to $C_4$-alkylene group,

C is a $C_1$- to $C_6$-alkylene group and

X is an anion; and adding said compound of formula (I) to said corrosive system as corrosion inhibitors.

2. The method as claimed in claim 1, in which A is an ethylene or propylene group.

3. The method as claimed in claim 1, in which C is a $C_2$-to $C_4$-alkylene group.

4. The method as claimed in claim 1, in which n is a number between 2 and 6.

5. The method as claimed in claim 1, in which R⁵ is an alkyl or alkenyl group having 2 to 24 carbon atoms.

6. The method as claimed in claim 1, in which R³ is an alkyl or alkenyl group having 2 to 12 carbon atoms.

7. The method as claimed in claim 1, in which R⁴ corresponds to a radical of the formula (4)

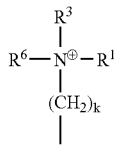  (4)

in which R⁶ is a radical of the formula

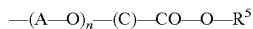  (3)

or $C_1$- to $C_{30}$-alkyl or $C_2$- to $C_{30}$-alkenyl and k is 2 or 3.

8. The method as claimed in claim 1, in which compounds of the formulae (5) or (8)

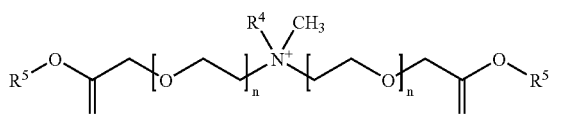  (5)

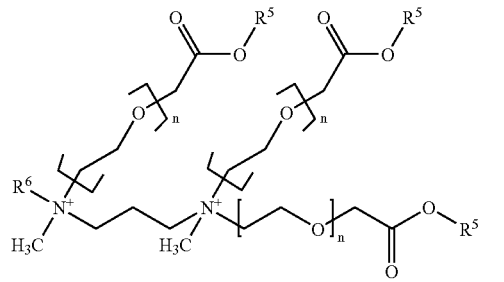  (8)

are used.

9. A compound of the formula (1),

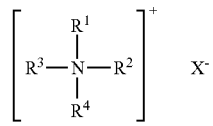  (1)

in which

R¹, R², is a radical of the formula

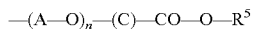  (3)

R³ is $C_1$- to $C_{30}$-alkyl or $C_2$- to $C_{30}$-alkenyl

R⁴ is an organic radical having 1 to 100 carbon atoms which does not contain a heteroatoms R⁵ is $C_1$- to $C_{30}$-alkyl or $C_2$- to $C_{30}$-alkenyl n is a number from 1 to 20

A is a $C_2$- to $C_4$-alkylene group,

C is a $C_1$- to $C_6$-alkylene group and

X is an anion.

10. The method as claimed in claim 1, in which said metal surfaces are iron-containing metals.

* * * * *